United States Patent
Atallah et al.

(10) Patent No.: US 11,366,027 B2
(45) Date of Patent: Jun. 21, 2022

(54) METHOD OF PREDICTING A STABILIZATION TEMPERATURE OF A HEAT-FLOW SENSOR

(71) Applicant: KONINKLIJKE PHILIPS N.V., Eindhoven (NL)

(72) Inventors: Louis Nicolas Atallah, Boston, MA (US); Patrick Zuidema, Mierlo (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 749 days.

(21) Appl. No.: 15/777,448

(22) PCT Filed: Dec. 12, 2016

(86) PCT No.: PCT/EP2016/080552
§ 371 (c)(1),
(2) Date: May 18, 2018

(87) PCT Pub. No.: WO2017/108459
PCT Pub. Date: Jun. 29, 2017

(65) Prior Publication Data
US 2018/0356298 A1   Dec. 13, 2018

(30) Foreign Application Priority Data
Dec. 21, 2015  (EP) .................................. 15201451

(51) Int. Cl.
*A61B 5/00*  (2006.01)
*G01K 13/20*  (2021.01)
(Continued)

(52) U.S. Cl.
CPC ................ *G01K 13/20* (2021.01); *A61B 5/01* (2013.01); *G01K 1/165* (2013.01); *G01K 7/42* (2013.01)

(58) Field of Classification Search
CPC ............ G01K 1/16; G01K 1/165; G01K 1/14; G01K 1/143; G01K 1/146; G01K 1/02;
(Continued)

(56) References Cited

U.S. PATENT DOCUMENTS 3,878,724 A * 4/1975 Allen ...................... G01K 7/42
374/169
4,341,117 A * 7/1982 Goldstein ............ G01K 13/002
374/170
(Continued)

FOREIGN PATENT DOCUMENTS

| CN | 101251501 A | 8/2008 |
|---|---|---|
| CN | 201697888 U | 1/2011 |
| WO | 2008078271 A1 | 7/2008 |

OTHER PUBLICATIONS

D.C Johnston, Stretched exponential relaxation arising from a continuous sum of exponential decays, Nov. 27, 2006, Physical Review B 74, 184430.*

(Continued)

*Primary Examiner* — May A Abouelela

(57) ABSTRACT

The invention describes a method of predicting a stabilization temperature ($T_\infty$) of a subject (8) with a heat-flow sensor (1) comprising a plurality of thermistors (S1, S2, S1A, S2A, S1B, S2B), which method comprises the steps of expressing the temperature development of the heat-flow sensor (1) as a stretched exponential equation characterized by a time constant ($\tau$) and a sensor characteristic scalar value (m); receiving temperature measurement values (T1, T2, T3, T4) collected by the thermistors (S1, S2, S1A, S2A, S1B, S2B); estimating the time constant ($\tau$) on the basis of the temperature measurement values (T1, T2, T3, T4); and deducing the future stabilization temperature ($T_\infty$) on the basis of the (Continued)

estimated time constant (τ). The invention further describes heat-flow sensor (1) and a temperature sensing arrangement (9).

12 Claims, 2 Drawing Sheets

(51) Int. Cl.
  *G01K 7/42* (2006.01)
  *A61B 5/01* (2006.01)
  *G01K 1/16* (2006.01)
(58) Field of Classification Search
  CPC ........ G01K 1/022; G01K 1/024; G01K 1/028; G01K 13/002; G01K 2007/422; G01K 3/04; G01K 13/20; G01K 7/42; A61B 5/01
  USPC ....................................................... 600/549
  See application file for complete search history.

(56) References Cited

U.S. PATENT DOCUMENTS

| | | | | |
|---|---|---|---|---|
| 4,574,359 A * | 3/1986 | Ishizaka | ................... | G01K 7/42 |
| | | | | 374/107 |
| 4,648,055 A * | 3/1987 | Ishizaka | ................... | G01K 7/42 |
| | | | | 374/107 |
| 4,811,198 A * | 3/1989 | Ota | ......................... | G01K 7/42 |
| | | | | 374/169 |
| 4,843,577 A * | 6/1989 | Muramoto | ............ | G01K 13/20 |
| | | | | 702/131 |
| 4,866,621 A * | 9/1989 | Ono | ........................ | G01K 7/42 |
| | | | | 600/549 |
| 5,011,294 A * | 4/1991 | Yamaguchi | ............. | G01K 7/42 |
| | | | | 374/107 |
| 5,015,102 A * | 5/1991 | Yamaguchi | ............. | G01K 7/42 |
| | | | | 374/107 |
| 6,439,768 B1 * | 8/2002 | Wu | ........................ | G01K 7/42 |
| | | | | 374/102 |
| 6,698,921 B2 * | 3/2004 | Siefert | ..................... | G01K 7/42 |
| | | | | 374/107 |
| 7,270,476 B2 * | 9/2007 | Tokita | ..................... | G01K 7/42 |
| | | | | 374/107 |
| 7,549,792 B2 * | 6/2009 | Bisch | ....................... | G01K 7/42 |
| | | | | 374/121 |
| 7,749,170 B2 * | 7/2010 | Waldhoff | ................ | A61B 5/01 |
| | | | | 600/549 |
| 7,785,266 B2 * | 8/2010 | Fraden | ................... | G01K 1/165 |
| | | | | 600/549 |
| 7,828,743 B2 * | 11/2010 | Fraden | ................... | G01K 1/165 |
| | | | | 600/549 |
| 8,197,128 B2 * | 6/2012 | Zhang | ................... | G01K 13/20 |
| | | | | 374/102 |
| 10,434,241 B2 * | 10/2019 | Hvid | ...................... | G01K 13/02 |
| 10,792,184 B2 * | 10/2020 | Hvid | ................... | A61M 3/0258 |
| 2006/0224349 A1 * | 10/2006 | Butterfield | ............... | G01K 7/42 |
| | | | | 702/130 |
| 2010/0169050 A1 | 7/2010 | Razzaghi | | |
| 2011/0072978 A1 * | 3/2011 | Popescu | ............ | A47G 19/2227 |
| | | | | 99/288 |
| 2011/0158284 A1 * | 6/2011 | Goto | ........................ | A61B 5/01 |
| | | | | 374/163 |
| 2012/0109572 A1 | 5/2012 | Shimizu | | |
| 2015/0247828 A1 | 9/2015 | Ruellan et al. | | |
| 2016/0054362 A1 * | 2/2016 | Tsubuku | ........... | H01L 29/78696 |
| | | | | 702/64 |
| 2016/0187272 A1 * | 6/2016 | Ishii | ........................ | G01K 7/42 |
| | | | | 702/136 |
| 2016/0302671 A1 * | 10/2016 | Shariff | ................... | G16H 50/50 |
| 2017/0079532 A1 * | 3/2017 | Larsen | ..................... | G01J 5/12 |
| 2017/0203122 A1 * | 7/2017 | Van Abeelen | ....... | A61N 5/0625 |
| 2017/0231490 A1 * | 8/2017 | Toth | ..................... | A61B 5/1075 |
| | | | | 600/558 |

OTHER PUBLICATIONS

International Search Report and Written Opinion, International Application No. PCT/EP2016/080552, dated Jan. 30, 2017.

* cited by examiner

METHOD OF PREDICTING A STABILIZATION TEMPERATURE OF A HEAT-FLOW SENSOR

This application is the U.S. National Phase application under 35 U.S.C. § 371 of International Application No. PCT/EP2016/080552, filed on Dec. 12, 2016, which claims the benefit of European Application Serial No. 15201451.0, filed Dec. 21, 2015. These applications are hereby incorporated by reference herein.

FIELD OF THE INVENTION

The invention relates to a method of predicting a stabilization temperature of a heat-flow sensor. The invention further relates to a heat-flow sensor and a temperature sensing arrangement.

BACKGROUND OF THE INVENTION

In healthy humans, core body temperature is usually maintained near a constant level in the range 36.5-37.5° C. by thermoregulation. The core body temperature can fluctuate slightly about this essentially constant level. However, a patient's core body temperature can decrease significantly in certain situations, for example during a surgical procedure in a cold operating theatre. Equally, some kinds of illness are accompanied by an increase in core body temperature. In any case, it is important to identify critical situations in which a patient's core body temperature is too low (hypothermia) or too high (hyperthermia). For this reason, a patient's temperature must be monitored continually. This has generally been done using thermometer probes such as oesophageal, rectal and urethral probes. Disadvantages of these probes are that they are intrusive and do not always deliver reliable results. A less intrusive approach is based on an active heat-flow sensor to measure a local heat flux density in a direction outward from the patient. An active heat-flow sensor uses a heat source and temperature sensors to estimate core body temperature on the basis of zero heat flux situation. However, this type of temperature sensor requires a heating element and a controller for the heating element, is relatively expensive, and requires a power supply that is capable of operating the heating element at all times. Such a temperature sensor is described in WO 2008/078271 A1, for example.

Another type of non-intrusive temperature measurement is achieved by a passive heat-flow sensor, which uses heat flow between one or more thermistor pairs to measure the temperature of a patient or subject. A first "inner" thermistor of a pair is located close to the patient's skin on one side of the sensor, and a second "outer" thermistor of the pair is located on the other side of the sensor and is separated from the inner thermistor by the sensor material, for example a synthetic material. The sensor is applied to the patient at a suitable location (e.g. on the skin over the carotid artery). Since the sensor is initially assumed to be cooler than the patient, the sensor measures heat flux in the outward direction, i.e. from the inner to the outer thermistor. The sensor will gradually heat up from its initial temperature until the inner thermistor reaches the same temperature as the patient. At this point, the temperature of the inner thermistor can be assumed to match the core body temperature of the patient.

A "single heat-flow" passive sensor uses one such thermistor pair. A "dual heat-flow" sensor uses two such thermistors pairs, with different material and/or different material thicknesses separating the inner and outer thermistors of the thermistor pairs. In each case, knowledge of the material properties of the sensor (e.g. thermal conductivity or its reciprocal, thermal resistivity), together with the temperature measurement values from the thermistor pairs allows the temperature of the subject to be determined with some accuracy. Heat-flow sensors have the advantage of being relatively economical, and can be realized as disposable products for use in a hospital environment. Furthermore, heat-flow sensors require very little power to operate. However, a passive single heat-flow sensor requires some expertise in placement and/or certain assumptions to be made regarding the area under the sensor. Incorrect placement may result in a misleading estimation of the core body temperature.

Another potential drawback related to using a passive heat-flow sensor is that it takes a relatively long time to heat up to a point at which the temperature throughout the sensor is essentially uniform, i.e. a "stabilization temperature". The heat-up time of a sensor depends to some extent on the surface area making contact with the skin. The heat-up time also depends on the thickness of the sensor and/or on the sensor material. For example, the thicker the layer between thermistors of a thermistor pair, the longer it takes for the sensor to heat up. This applies particularly to the dual heat-flow sensor type, for which one of the thermistor pairs is separated by a greater layer thickness. The heat-up time of a dual heat-flow sensor can be twice as long as a comparable single heat-flow sensor. The long heat-up time of a heat-flow sensor may be unacceptable or problematic in certain circumstances such as emergency situations or any situation in which a prompt core body temperature reading is required.

For example, it can be very important in some situations to quickly determine a patient's core body temperature, particularly if a patient is already hypothermic, which may be the case upon admission to an accident and emergency unit, or if a patient is at risk from hypothermia during surgery in a cold operating theatre. A long heat-up time is unacceptable in such a situation, since critical decisions may need to be made, based on an accurate knowledge of the patient's thermal condition.

Therefore, it is an object of the invention to provide an improved way of determining the core body temperature of a patient.

SUMMARY OF THE INVENTION

The object of the invention is achieved by the method of claim 1 of predicting a core body temperature of a subject by means of a passive heat-flow sensor; by the passive heat-flow sensor of claim 9; and by the temperature sensing arrangement of claim 10 for monitoring the temperature of a subject.

According to the invention, the method comprises the steps of expressing the temperature development of the passive heat-flow sensor as a stretched exponential equation characterized by a time constant and a sensor characteristic scalar value; receiving temperature measurement values collected by the thermistors; estimating the time constant on the basis of the temperature measurement values; and deducing the future stabilization temperature on the basis of the estimated time constant.

An advantage of the inventive method is that a rapid prediction of the core body temperature can be obtained well before the sensor has finished warming up. In the context of the invention, the expressions "stabilization temperature" and "core body temperature" are to be understood to mean the sensed temperature of the subject when heat-flow in the sensor has reached an equilibrium state. The inventive method allows this stabilization temperature to be predicted long before it is actually reached by the sensor. In other words, even if the heat-flow sensor has a relatively long heat-up time, this is no longer a disadvantage, since the sensor can report an accurate estimation of the stabilization temperature, i.e. a predicted core body temperature, even while the sensor is still heating up.

According to the invention, the passive heat-flow sensor comprises at least one thermistor pair, with an inner thermistor at an inner face of the heat-flow sensor and an outer thermistor at an outer face of the heat-flow sensor; an evaluation unit arranged to receive temperature measurement values from the thermistors and to predict a core body temperature of a subject using the inventive method; and a user interface arranged to show the predicted stabilization temperature.

In the context of the invention, the location of a thermistor "at a face of the sensor" is to be understood to mean that the thermistor is close to that face. For example, the outer thermistor being placed "at an outer face" of the sensor is to be understood to mean that the outer thermistor of a thermistor pair is arranged further outward relative to the inner thermistor of that pair. The inner thermistor is then closest to the contact face of the sensor, while the outer thermistor is furthest from the contact face. A thermistor can be partially or completely enclosed by the material of the sensor, i.e. with a layer of sensor material between the thermistor and the outside. Such an arrangement can favorably insulate the outer thermistor from the outside environment, and thus shorten the heat-up time of the sensor. An advantage of the inventive heat-flow sensor is that it can report an accurate estimation of the future stabilization temperature even while the sensor is heating up towards that stabilization temperature, so that a user of the sensor does not need to wait for the entire heat-up time before being given an estimate of the future stabilization temperature.

According to the invention, the temperature sensing arrangement comprises a heat-flow sensor with at least one thermistor pair comprising an inner thermistor at an inner face of the heat-flow sensor and an outer thermistor at an outer face of the heat-flow sensor; and an evaluation unit arranged to receive temperature measurement values from the thermistors and to predict a core body temperature of a subject using the inventive method.

An advantage of the inventive temperature sensing arrangement is that an accurate core body temperature can be reported to a user of the sensor before the sensor has warmed up.

The dependent claims and the following description disclose particularly advantageous embodiments and features of the invention. Features of the embodiments may be combined as appropriate. Features described in the context of one claim category can apply equally to another claim category.

It shall be understood that the stabilization temperature, as described in the introduction, is not necessarily constant. The core body temperature of a patient can fluctuate due to the physiology of the patient, and can also depend on the time of day. Furthermore, a patient's core body temperature can decrease significantly in certain situations, for example during a surgical procedure in a cold operating theatre. Equally, some kinds of illness are accompanied by a significant increase in core body temperature. In any case, it is important to identify critical situations in which a patient's core body temperature is too low (hypothermia) or too high (hyperthermia).

The inventive temperature sensor can be used to quickly obtain a steady-state temperature reading for any subject. In the following, without restricting the invention in any way, the term "subject" shall be understood to mean any living being, for example a human patient whose temperature is to be monitored peri-operatively. The terms "subject" and "patient" may be used interchangeably in the following, similarly the expressions "core body temperature", "steady-state temperature" and "stabilization temperature" are synonymous and may be used interchangeably. The terms "heat flux" and "heat-flow" are synonymous and may be used interchangeably in the following. A "passive sensor" may simply be referred to as a "sensor" in the following.

The inventive sensor can be realized in any suitable manner. For example, in a straightforward realization, the temperature sensor comprises a single thermistor pair, with a first or inner thermistor arranged to be in close proximity with the surface of the subject (for example the patient's skin) and a second or outer thermistor arranged at the opposite side of the sensor. In this way, the thermistors are separated by a certain thickness of the sensor material. The temperature registered by the outer thermistor will depend on the thermal resistivity of the sensor material and also on the temperature registered by the inner thermistor. A heat flux sensor with a single thermistor pair is referred to as a single heat-flow sensor.

Obtaining a temperature measurement at any one point in time using a heat-flow sensor involves collecting the temperature measurement values from the thermistors, and calculating the sensed temperature using knowledge of the sensor material. For a single heat-flow sensor, the sensed body temperature $T_B$ at any one measurement instant may be expressed as follows:

$$T_B = T1 + \frac{R_B}{R1}(T1 - T2) \tag{1}$$

where T1 is the temperature measurement value provided by the inner thermistor (e.g. in contact with the patient's skin), and T2 is the temperature measurement value provided by the outer thermistor; R1 is the thermal resistivity of the material from which the sensor is made, and $R_B$ is the thermal resistivity of the body, for example taking into account the thermal resistivity of the patient's skin and other tissue. Therefore, to accurately compute the sensed temperature using a single heat-flow sensor, some knowledge of the thermal resistivity of the skin is required. This can vary from patient to patient.

In a further preferred embodiment of the invention, the temperature sensor comprises two or more thermistor pairs, each with an inner thermistor arranged to be in close proximity with the surface of the subject and an outer thermistor arranged at the opposite side of the sensor. A heat flux sensor with two or more such thermistor pairs is referred to as a dual heat-flow sensor or dual sensor. The thermistors of the pairs can be separated by different layer thicknesses. For example the sensor can be thicker in the middle, so that the thermistors of a centrally positioned thermistor pair can be separated by a thick layer of sensor material, while the thermistors of another pair—positioned further outwards—are separated by a thinner layer.

The body temperature $T_B$ sensed at any one measurement instant by a dual heat-flow sensor may be expressed as follows:

$$T_B = \frac{T1 \cdot R1(T3 - T4) - T3 \cdot R2(T1 - T2)}{R1(T3 - T4) - R2(T1 - T2)} \quad (2)$$

where T1, T2 are the temperature measurement values provided by the inner and outer thermistors respectively of the first thermistor pair; T3, T4 are the temperature measurement values provided by the inner and outer thermistors respectively of the second thermistor pair; R1 is the thermal resistivity of the thicker layer between the thermistors of the first thermistor pair, and R2 is the thermal resistivity of the thinner layer between the thermistors of the second thermistor pair. The dual heat-flow sensor does not require any knowledge of the thermal resistivity of the patient's skin.

A thermistor is a device whose electrical resistivity changes in response to a change in temperature. A temperature change is registered as a change in current or voltage, depending on the circuit realization. A thermistor can be realized as a compact integrated circuit (IC) device. Such devices can be embedded in the material of the sensor. In one preferred embodiment of the invention, the thermistors can be connected via wire connections to an evaluation unit. For example, temperature measurement values can be received by an evaluation unit connected to the sensor by a cable connection. In another preferred embodiment of the invention, the sensor can be equipped with an interface for transmitting the temperature measurement values wirelessly to the evaluation module. The sensor may also incorporate an analog-to-digital converter to convert analogue measurement values into digital values for data transmission. In another preferred embodiment of the invention, the sensor itself can comprise the evaluation unit and a display that indicates the sensed temperature of the patient or subject. Such a display can be realized as an LED display, for example to show the sensed temperature in degrees Celsius. An LED display can also provide visual feedback regarding the sensed temperature, for example by using a green color to indicate that the sensed temperature is in a satisfactory or safe zone, a red color to indicate a potentially dangerous low or high level, etc.

In a further preferred embodiment of the invention, an evaluation unit is realized as a portable device. For example, a handheld device such as a mobile phone or tablet generally has a display, which can be used to show the predicted steady-state temperature shortly after the sensor is applied to the patient, and also to show the actual temperature development.

When a heat-flow sensor is placed on a warmer body, for example by an adhesive patch, the temperature of the sensor will increase until it reaches the same temperature as the body to which it is attached. The development of the temperature measured by the heat-flow sensor can be regarded as a response to a step function with an abrupt change from the initial temperature $T_0$ to a final steady-state temperature $T_\infty$ (i.e. the core body temperature of the patient). At that point, the temperature difference between inner and outer thermistors becomes constant. This situation indicates that the stabilization temperature has been reached. When used to monitor a patient's temperature, the temperature will generally fluctuate only slightly about this otherwise essentially constant stabilization temperature. The inventive method is based on the insight that, as the sensor heats up from an initial starting temperature, the temperature development will follow a stretched exponential equation. In the context of the invention, the term "temperature development" is to be understood to mean a curve defined by the sequence of sensed temperatures reported by the sensor once it has been placed on the subject. As indicated above, one of the factors relevant to the temperature development is the initial temperature of the sensor. Therefore, in a particularly preferred embodiment of the invention, the temperature development is also expressed in terms of the initial temperature. According to the invention, the temperature T(t) reported by the sensor can be expressed by the stretched exponential equation:

$$T(t) = T_\infty + (T_0 - T_\infty)e^{-\left(\frac{t}{\tau}\right)^m} \quad (3)$$

where $T_0$ is the initial temperature of the sensor, $T_\infty$ is the stabilization or core body temperature of the subject, $\tau$ is a time constant of the stretched exponential, and m is a scalar whose value is determined by a sensor characteristic property, for example the thermal resistivity of the sensor, which in turn is governed by the material and the sensor thickness between inner and outer thermistors. The exponent term in equation (3) is itself also an exponent:

$$-\left(\frac{t}{\tau}\right)^m \quad (3a)$$

For any value of m, a graph of equation 3 will pass through a point whose x-coordinate is the time constant $\tau$. The inventive method expresses the temperature as the stretched exponential of equation (3), and certain mathematical properties of this expression allow significant deductions to be made, as will be explained below.

The initial temperature $T_0$ can be measured directly and is therefore a known quantity. It remains to determine values for $\tau$ and m in order to solve for the stabilization temperature $T_\infty$. In a preferred embodiment of the invention, the method comprises the steps of identifying a first relationship as a function of the time constant and the sensor characteristic, and a second relationship as a function of the time constant and the sensor characteristic, and subsequently solving the first and second relationships to determine the time constant and the sensor characteristic so that these can be inserted into the stretched exponential equation to predict the stabilization temperature.

One property of the stretched exponential of equation (3) is that the slope of the curve is initially steep, and gradually flattens off to approach the stabilization temperature. The slope, i.e. the first derivative of equation (3) is:

$$T'(t) = -\frac{m}{\tau}\left(\frac{t}{\tau}\right)^{m-1}(T_0 - T_\infty)e^{-\left(\frac{t}{\tau}\right)^m} \quad (4)$$

It is known than the first derivative will be zero at a maximum of the first derivative. Therefore, in a preferred embodiment of the invention, the first relationship expresses the corresponding time as a function of the time constant and the sensor characteristic:

$$t_{max} = \tau\left(\frac{m-1}{m}\right)^{\frac{1}{m}} \quad (5)$$

where $t_{max}$ is the time at which equation (4) reaches its maximum. In order to solve for the two unknowns τ and m, a second equation or relationship is required. In a further preferred embodiment of the invention, a suitable candidate can be a ratio R of the first derivatives at any two arbitrary instances along the X-axis, which ratio is expressed as:

$$R = \frac{(u/\tau)^{m-1} e^{-(u/\tau)^m}}{(v/t)^{m-1} e^{-(v/\tau)^m}} \qquad (6)$$

where u, v are time values along the X-axis. The two equations (5) and (6) allow to solve for the two unknowns τ and m. These can then be inserted into equation (3), which can then be solved for the core body temperature $T_\infty$. Since the inventive method can predict the patient's core body temperature essentially as soon as the slope of the temperature development stops increasing (this point corresponds to a maximum of the first derivative of equation (3)), it is possible to achieve a reliable estimate of the core body temperature well before the sensor has warmed up.

In a first practical embodiment, once the sensor is in place, the thermistor can start collecting temperature values at intervals (e.g. one measurement per second, per millisecond, or at any suitable sampling rate). A sensed temperature is computed from the measurement values of each sample, and the first few results can be averaged to obtain an initial sensed temperature $T_0$. Further temperature measurement values are collected and the sensed temperature is computed for each sample. By collecting these temperature measurement values, the first derivative of equation (3) can be estimated by calculating the difference between consecutive measurements. Initially, the sign of the first derivative will be positive. During this stage, time instants u and v are chosen and the ratio of the first derivative for these points is calculated, giving R in equation (6). The sign of the first derivative is observed. Ultimately, there will be a change in sign from positive to negative. This point in time marks the maximum of the first derivative of equation (3), and gives a value of $t_{max}$ for equation (5). The values of R and $t_{max}$ can then be used to consult a look-up table that returns two candidate values for τ and m. At the estimated time instant τ, the temperature T(τ) is measured. This value can then be inserted into equation (3'), yielding an estimation of the stabilization temperature $T_\infty$. In this embodiment, a reliable estimation or prediction of the stabilization temperature can be achieved within only a few minutes. This rapid prediction compares favorably to the prior art sensors, which can often need more than ten minutes to obtain a reliable reading, i.e. to report the sensed stabilization temperature.

Alternatively, another characteristic property of the stretched exponential equation can be used to predict the core body temperature. It is known that equation (3) defines a family of curves for different values of m, and that each m curve passes through a point at time τ. Therefore, in a further preferred embodiment of the invention, the method comprises a step of fitting a number of curves to the sensed temperatures for different values of m. For example, for various values of m, a curve-fitting algorithm can be applied to the temperature values already measured by the sensor in order to achieve a fitted curve. In a further preferred embodiment of the invention, the method includes a step of identifying the time constant τ from an intersection point of a plurality of fitted curves and subsequently solving the stretched exponential equation to predict the stabilization temperature. At time τ, the exponent in Equation (3a) reduces to −1, allowing the core body temperature $T_\infty$ to be computed directly from the following simplified version of equation (3):

$$T(\tau) = T_\infty + (T_0 - T_\infty) e^{-1} \qquad (3')$$

The steps of curve-fitting and determining the intersection point can be performed with relatively little effort using known mathematical tools. The sensor can start collecting temperature values as soon as it is in place. At intervals, the set of previously measured values is fed to a curve-fitting algorithm. Therefore, each successive curve-fitting step is finer than the previous step. Once two or more curves have been fitted, their intersection is determined. The corresponding x-coordinate yields time τ. The temperature T(τ) measured at time τ can simply be used in equation (5) to yield the core body temperature $T_\infty$. In this embodiment also, a reliable estimation or prediction of the core body temperature $T_\infty$ can be achieved within only a few minutes.

Other objects and features of the present invention will become apparent from the following detailed descriptions considered in conjunction with the accompanying drawings. It is to be understood, however, that the drawings are designed solely for the purposes of illustration and not as a definition of the limits of the invention.

BRIEF DESCRIPTION OF THE DRAWINGS

In the drawings, like numbers refer to like objects throughout. Objects in the diagrams are not necessarily drawn to scale.

DETAILED DESCRIPTION OF THE EMBODIMENTS

Figure 1:
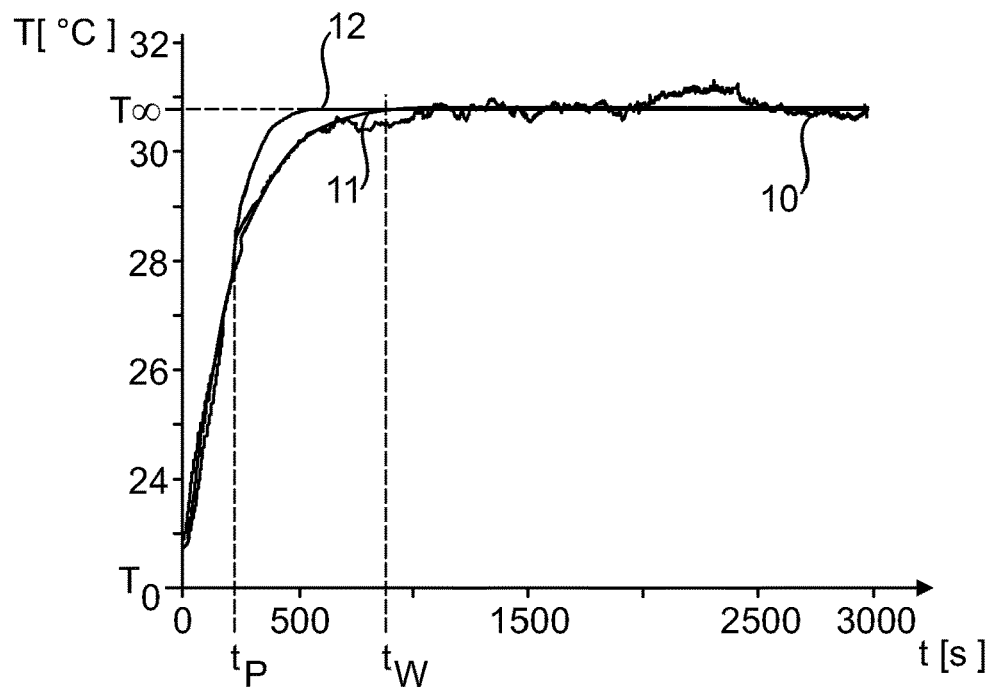
FIG. 1 shows temperature development in a heat-flow sensor applied to a subject and a curve fitted to a stabilization temperature predicted using the inventive method.

FIG. 1 shows experimental data illustrating the closeness of the inventive approach to the actual development of temperature in a heat-flow sensor applied to a subject. The diagram shows a graph 10 of sensed temperatures, commencing at an initial temperature $T_0$; a second graph 11 obtained by ex-post curve fitting applying the least squares method to the complete set of sensed temperatures; and a third graph 12 obtained using the method according to the invention, requiring only temperature measurement values collected up until the estimated time constant τ. The diagram clearly shows that the predicted stabilization temperature $T_\infty$ is essentially identical to the plateau of the fitted curve 11, showing that the predicted core body temperature $T_\infty$ is a very close match to the actual "steady-state" temperature of the subject. A prior art passive heat-flow sensor must first finish warming up in order to report the sensed core body temperature. This can take a relatively long time, shown here at time $t_w$ after about 13 minutes. In contrast, the core body temperature predicted by the inventive method can be provided in a much shorter time $t_p$, since the prediction can be made as soon as the temperature development can be analyzed to determine the maximum of the derivative, or to determine the intersection point of a fitted curve family, using one of the inventive methods described above. The core body temperature can be predicted reliably after a favorably short interval of only a few minutes.

Figure 2:
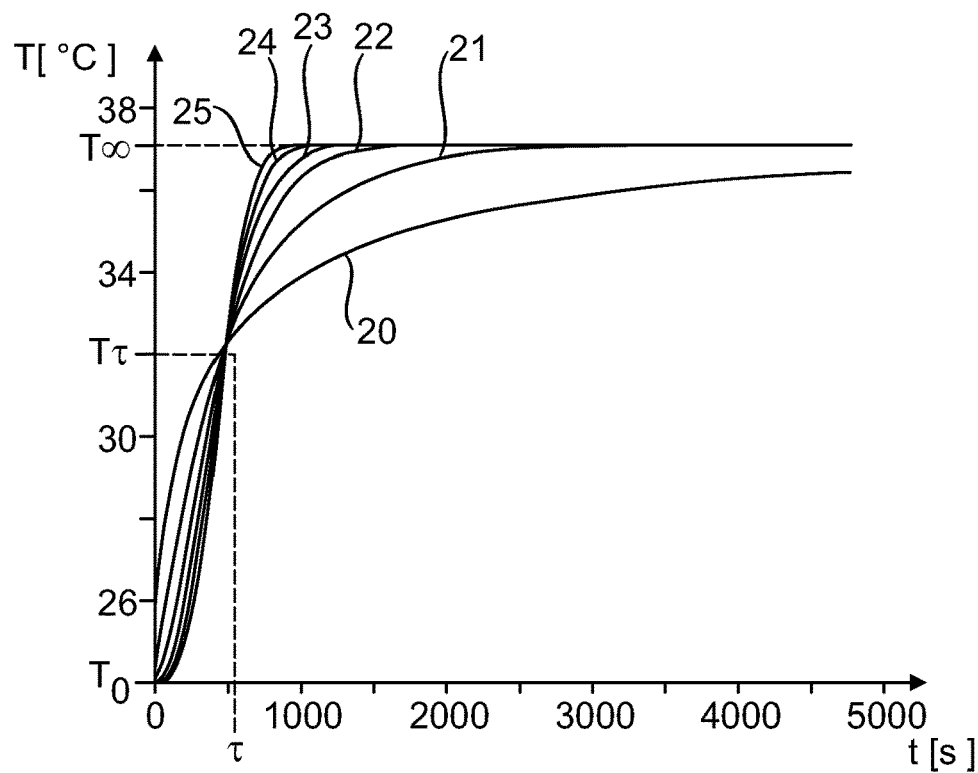
FIG. 2 shows a family of six fitted curves determined by applying an embodiment of the method according to the invention.

FIG. 2 illustrates the second approach described above, and shows a family of six fitted curves 20-25 for equation (3) with different values of m, obtained by curve-fitting to an initial set of measured temperature values. The flattest fitted curve 20 corresponds to m=0.5, while the steepest fitted curve 25 was obtained for m=3.0. The curves intersect at a point whose x-coordinate is the time constant $\tau$. Once this intersection point is determined, a temperature measurement value $T_\tau$ can be obtained for that time instant $\tau$. Knowing the initial temperature $T_0$, equation (3') can then be solved for the core body temperature $T_\infty$.

Figure 3:
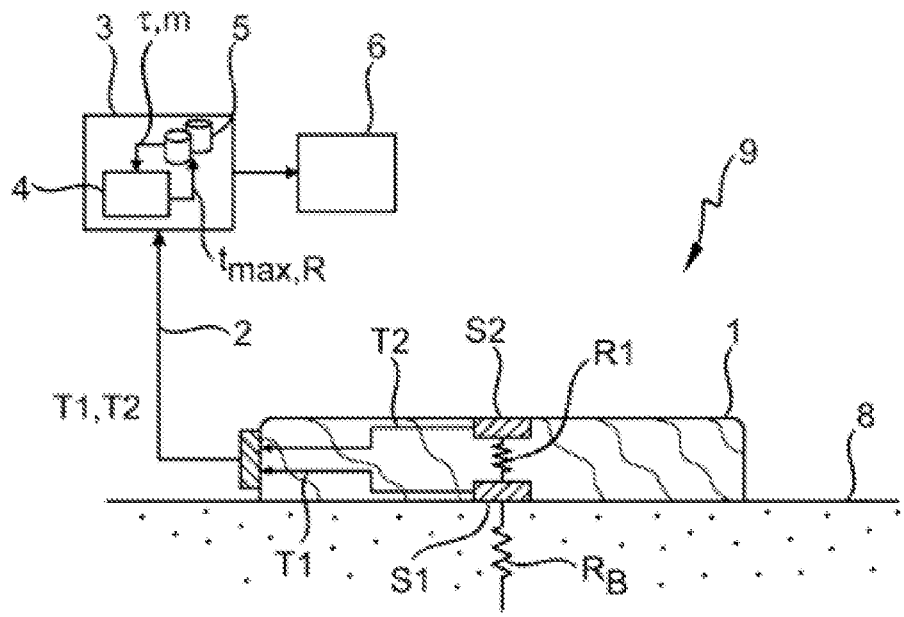
FIG. 3 shows a heat-flow sensor according to a first embodiment of the invention.

FIG. 3 shows a temperature sensing arrangement 9 according to a first embodiment of the invention, in which the heat-flow sensor 1 is realized as a single heat-flow sensor 1. This can be securely attached to the subject 8, for example to the skin of a patient 8. A first thermistor S1 is arranged at an inner face of the sensor 1, and will lie in close contact to the patient's skin. A second thermistor S2 is arranged at the outer surface of the sensor 1. The thermal resistivity R1 of the sensor 1 is indicated by the resistor symbol. A further resistor symbol indicates the thermal resistivity $R_B$ of the body to which the sensor 1 is attached.

Obtaining a sensed temperature at any one point in time using the sensor 1 involves collecting the temperature measurement values T1, T2 from the thermistors S1, S2, and calculating a sensed temperature using knowledge of the heat flux through the sensor 1. To compute the sensed temperature using the single heat-flow sensor, it is also necessary to determine or estimate the thermal resistivity of the skin, which may vary from patient to patient. The sensed body temperature may be calculated using equation (1) as already described above. To this end, the measurement values collected by the thermistors S1, S2 are sent to an evaluation unit 3 via a cable 2. A microprocessor 4 of the evaluation unit 3 performs the necessary computations, for example to estimate the time $t_{max}$ at which the first derivative reaches a maximum, and to compute a ratio R of first derivatives. For the computed values of time $t_{max}$ and first derivatives ratio R, a look-up-table 5 can supply candidate values for the time constant $\tau$ and the sensor characteristic value m. This allows equation (3) to be solved for the core body temperature $T_\infty$. Of course, the microprocessor can also be programmed to carry out the curve-fitting approach in order to identify the intersection point and the time constant $\tau$ as described above. A display 6 can show the predicted core body temperature $T_\infty$ as soon as this has been determined (at about time $\tau$), and also the actual temperature development curve 10 (as shown in FIG. 1) as time progresses.

Figure 4:
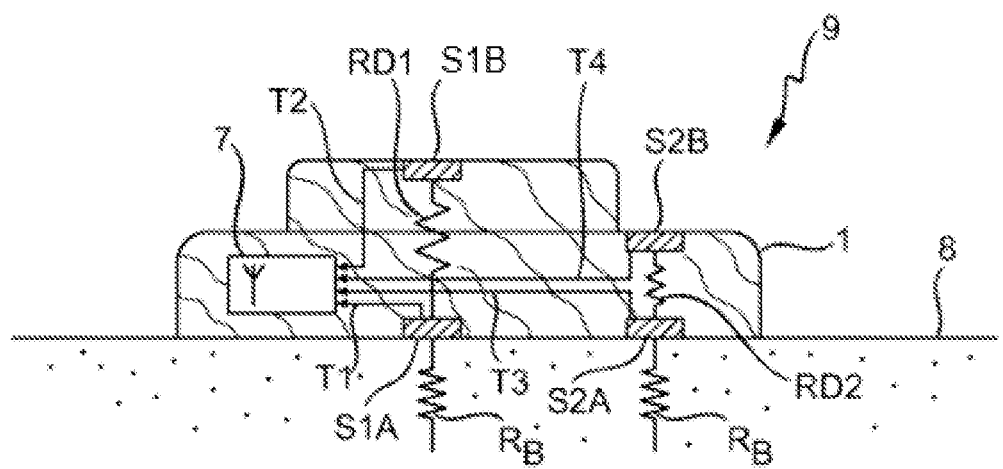
FIG. 4 shows a heat-flow sensor according to a second embodiment of the invention.

FIG. 4 shows a temperature sensing arrangement 9 according to a second embodiment of the invention, with a dual heat-flow sensor 1. Here, the first thermistor S1A of a first thermistor pair and the first thermistor S2A of a second thermistor pair are arranged at the inner face of the sensor 1, and will lie in close contact to the patient's skin. The second thermistor S1B of the first thermistor pair and the second thermistor S2B of the second thermistor pair are arranged at the outer surface of the sensor 1. The thermal resistivity RD1 between the thermistors of the first thermistor pair S1A, S1B, and the thermal resistivity RD2 between the thermistors of the second thermistor pair S2A, S2B are indicated by the resistor symbols. A further resistor symbol indicates the thermal resistivity $R_B$ of the body to which the sensor 1 is attached, but it is not necessary to actually know this value when using a dual heat-flow sensor.

Here also, obtaining a temperature measurement at any one point in time using the sensor 1 involves collecting the temperature measurement values from the thermistors S1A, S1B, S2A, S2B and calculating a sensed temperature using knowledge of the heat flux through the sensor 1. A sensed temperature measurement may be calculated using equation (2) as already described above. In this embodiment, the thermistors feed their values to an interface 7. This can include an evaluation unit as described in FIG. 3 above and a wireless interface for sending the predicted core body temperature T and the sensed temperatures over a wireless connection to a display. Alternatively, the interface 7 can simply transmit the temperature measurement values T5, T6, T3, T4 to an external evaluation unit for analyzing the measured temperature values T5, T6, T3, T4 to compute the sensed temperature for each sample, and to predict the core body temperature as described above. Of course, the sensor can be realized to include an evaluation unit as well as a display, as described above.

Although the present invention has been disclosed in the form of preferred embodiments and variations thereon, it will be understood that numerous additional modifications and variations could be made thereto without departing from the scope of the invention.

For the sake of clarity, it is to be understood that the use of "a" or "an" throughout this application does not exclude a plurality, and "comprising" does not exclude other steps or elements. The mention of a "unit" or a "module" does not preclude the use of more than one unit or module.

The invention claimed is:

1. A method of predicting a future stabilization temperature of a subject by means of a heat-flow sensor comprising a plurality of thermistors, which method comprises the steps of:

receiving temperature measurement values collected by the thermistors,
wherein the thermistors include at least a first thermistor pair and a second thermistor pair,
wherein the first thermistor pair includes a first inner thermistor at an inner face of the heat-flow sensor and a first outer thermistor at an outer face of the heat-flow sensor, wherein the first inner thermistor and the first outer thermistor are separated from each other by a first material thickness,
wherein the second thermistor pair includes a second inner thermistor at the inner face of the heat-flow sensor and a second outer thermistor at the outer face of the heat-flow sensor, wherein the second inner thermistor and the second outer thermistor are separated from each other by a second material thickness, and
wherein the first and second material thickness are different from each other;

fitting a plurality of curves to the received temperature measurement values, wherein each of the plurality of curves is associated with different characteristics of a sensor;

identifying an intersection point of the fitted curves;

determining a time constant based on the intersection point;

applying the time constant to a stretched exponential equation,
wherein the stretched exponential equation expresses a temperature development of the heat-flow sensor, and wherein applying the stretched exponential equation using the time constant predicts the future stabilization temperature.

2. The method according to claim 1, wherein the stretched exponential equation is further expressed in terms of an initial temperature.

3. The method according to claim 1, further comprising averaging an initial set of temperature measurement values to estimate an initial temperature.

4. The method according to claim 1, further comprising:
approximating a first derivative of the stretched exponential equation on a basis of the received temperature measurement values; and
identifying a maximum of the first derivative of the stretched exponential equation.

5. The method according to claim 4, further comprising:
identifying a first relationship relating to the maximum of the first derivative of the stretched exponential equation in terms of the time constant and one or more sensor characteristics of the heat-flow sensor; and
identifying a second relationship expressing a ratio of two values of the first derivative of the stretched exponential equation in terms of the time constant and the one or more sensor characteristics.

6. The method according to claim 5, further comprising solving the first and second relationships to determine the time constant and the one or more sensor characteristics, and subsequently solving the stretched exponential equation to predict the stabilization temperature.

7. The method according to claim 1, further comprising:
computing a temperature on a basis of the temperature measurement values; and
subsequently solving the stretched exponential equation to predict the stabilization temperature.

8. A heat-flow sensor comprising a first thermistor pair, with a first inner thermistor at an inner face of the heat-flow sensor and a first outer thermistor at an outer face of the heat-flow sensor; a second thermistor pair, with a second inner thermistor at the inner face of the heat-flow sensor and a second outer thermistor at the outer face of the heat-flow sensor; and an evaluation unit arranged to receive temperature measurement values from the first thermistor pair and the second thermistor pair, and to predict a future stabilization temperature of a subject by:
receiving temperature measurement values collected by the first thermistor pair and the second thermistor pair,
wherein the first inner thermistor and the first outer thermistor are separated from each other by a first material thickness,
wherein the second inner thermistor and the second outer thermistor are separated from each other by a second material thickness, and
wherein the first and second material thickness are different from each other;
fitting a plurality of curves to the received temperature measurement values, wherein each of the plurality of curves is associated with different characteristics of a sensor;
identifying an intersection point of the fitted curves;
determining a time constant based on the intersection point;
applying the time constant to a stretched exponential equation,
wherein the stretched exponential equation expresses a temperature development of the heat-flow sensor, and
wherein applying the stretched exponential equation using the time constant predicts the future stabilization temperature.

9. A temperature sensing arrangement for monitoring a temperature of a subject, comprising a heat-flow sensor with a first thermistor pair comprising a first inner thermistor at an inner face of the heat-flow sensor and a first outer thermistor at an outer face of the heat-flow sensor; a second thermistor pair comprising a second inner thermistor at the inner face of the heat-flow sensor and a second outer thermistor at the outer face of the heat-flow sensor; and an evaluation unit arranged to receive temperature measurement values from the first thermistor pair and the second thermistor pair, and to predict a future stabilization temperature ($T_\infty$) of the subject by:
receiving temperature measurement values collected by the first thermistor pair and the second thermistor pair,
wherein the first inner thermistor and the first outer thermistor are separated from each other by a first material thickness,
wherein the second inner thermistor and the second outer thermistor are separated from each other by a second material thickness, and
wherein the first thermistor pair includes a first inner thermistor and a first outer thermistor,
wherein the second thermistor pair includes a second inner thermistor and a second outer thermistors, and
wherein the first and second material thickness are different from each other;
fitting a plurality of curves to the received temperature measurement values, wherein each of the plurality of curves is associated with different characteristics of a sensor;
identifying an intersection point of the fitted curves;
determining a time constant based on the intersection point;
applying the time constant to a stretched exponential equation,
wherein the stretched exponential equation expresses a temperature development of the heat-flow sensor, and
wherein applying the stretched exponential equation using the time constant predicts the future stabilization temperature.

10. The temperature sensing arrangement according to claim 9, further comprising a cable connection between the heat-flow sensor and the evaluation unit.

11. The temperature sensing arrangement according to claim 9, wherein the heat-flow sensor further comprises a wireless interface for transmitting the temperature measurement values to the evaluation unit.

12. The temperature sensing arrangement according to claim 9, wherein the evaluation unit is a portable device.

* * * * *